United States Patent [19]

Conway et al.

[11] Patent Number: 4,767,623
[45] Date of Patent: Aug. 30, 1988

[54] METHOD OF BINDING MICROFLORA AND PREPARATIONS THEREFOR

[75] Inventors: Patricia Conway; Staffan Kjelleberg, both of Södra Vägen, Sweden

[73] Assignee: Chemical Dynamics Sweden AB, Skara, Sweden

[21] Appl. No.: 882,897
[22] PCT Filed: Nov. 5, 1985
[86] PCT No.: PCT/SE85/00431
§ 371 Date: Jul. 8, 1986
§ 102(e) Date: Jul. 8, 1986
[87] PCT Pub. No.: WO86/02837
PCT Pub. Date: May 22, 1986

[30] Foreign Application Priority Data

Nov. 8, 1984 [SE] Sweden ................. 8405587

[51] Int. Cl.$^4$ ............................. A61K 37/00
[52] U.S. Cl. ........................ 424/93; 514/2; 435/243; 435/245; 435/853
[58] Field of Search ................... 424/93; 514/2

[56] References Cited

U.S. PATENT DOCUMENTS 3,320,130  5/1967  Henry ..................... 424/93
3,713,836  1/1973  Carlsson et al. .
4,314,995  2/1982  Hata et al. ................ 424/93
4,332,790  6/1982  Sozzi et al. .

FOREIGN PATENT DOCUMENTS 033584   8/1981  European Pat. Off. .
2010654  5/1971  Fed. Rep. of Germany .
2738652  3/1979  Fed. Rep. of Germany .
8401713  5/1984  PCT Int'l Appl. .
637297   7/1983  Switzerland .

OTHER PUBLICATIONS

Livsmedels Teknik, vol. 24, No. 9, pp. 434–436.
Japanese Patents Report, vol. 84, No. 48, 1985, (Derwent Publications Ltd, London), Section CH: Chemical, J8-C, No. J8 4 046 209-B, pub. 1984-11-10.

*Primary Examiner*—Sam Rosen
*Attorney, Agent, or Firm*—Dennison, Meserole, Pollack & Scheiner

[57] ABSTRACT

The adhesion of non-pathogenic bacteria to the stomach and intestines of humans and animals is increased by the administration of the bacteria in the presence of a protein, designated adhesive promoting protein, which can be produced by cultivating lactic acid bacteria in a medium with the addition of forms of sugar of enhanced concentration. A preparation to increase said adhesion contains non-pathogenic bacteria cultivated in the manner described above, together with adhesive promoting protein.

11 Claims, No Drawings

METHOD OF BINDING MICROFLORA AND PREPARATIONS THEREFOR

The present invention relates to a method for microbial colonisation of the oesophagus, stomach and intestines of animals and humans by utilizing bacteria beneficial to the host organism. The invention also relates to a method strengthening the mechanism for adhesion of desired species of bacteria applied. The invention also relates to preparations for achieving the results mentioned above.

The invention will be described and is applicable for both animals and humans. "Animals" here relates to domestic animals such as pigs, calves and poultry, such as chickens, turkeys, geese and ducks.

At present the mortality rate amongst the above-mentioned animals is high, and is caused by the establishment and colonisation of pathogenic bacteria in the stomach and intestines. Pathogenic bacteria out compete the normal bacteria flora, adhere to the wall of the intestines and give rise to symptoms of disease such as diarrhoea, and results in increased mortality. The losses in some herds or flocks are considerable as a result of outbreaks of pathogenic bacteria as *Escherichia coli*, *Salmonella typhimurium*, Salmonella sp., Shigella sp. and *Clostridium perfringens*.

Numerous attempts are currently being made to introduce nonpathogenic bacteria into the gastro intestinal tract in order to prevent or remove colonisation of pathogenic bacteria. Oral administration of different types of bacillus to humans has been found to reduce the risk of cancer in the large intestine and increase the removal or ousting of intestinal pathogens as well as being of therapeutic value of elderly patients. Equivalent studies of animals and humans have the common factor that bacteria introduced in the gastro intestinal tract in order to improve the state of health and increase survival in the host organism. Colonisation of these bacteria is possible provided the bacteria cells are capable of attaching themselves to the epithelium walls of the host organism.

An almost continuous supply of large bacteria cultures is required to achieve the above results, which makes the method impractical.

Most studies of the above type have been carried out on animals and show negative results with respect to adhesion and colonisation of the specific type of bacteria used. Existing methods have the following problems, which also prevent successful experiments:
1. Administering bacteria strains of non-specific type which do not exhibit selective colonisation or survival.
2. Administering bacterial strains whose adhesion ability has been investigated and determined in in vitro experiments. The limitation here is that the mechanism for adhesion is not defined and specific (lectin-mediated) binding cannot be determined.

Some examples illustrate these limitations:
In pigs:
1. Lactobacillus acidophilus from foodstuff was administered in the normal manner.
2. Lactobacillus sp. which had been isolated from the animal was administered orally. Colonisation was not obtained in either case.

In humans:
3. *Lactobacillus acidophilus* and *L. bulgaricus* were administered orally and initially showed favourable results, but without colonisation being obtained. The results usually disappeared after 3 days, a decline which accords well with the reduction in the number of Lactobacillus cells in the host organism.

In research into the adhesion of lactic acid bacteria e.g. the genera Lactobacillus and Streptococcus to the gastro intestinal tract in laboratory animals it was found contrary to accepted belief, that the specific binding of the bacteria to epithelial cells in the host organism, is not mediated by polysaccharides, but rather by a protein.

The following points constitute the bases of the process on which the present invention is founded:
(a) The mechanism for specific binding of lactic acid bacteria e.g. the genera Lactobacillus and Streptococcus to the oesophagus and gastro intestinal tract consists of an extracellular protein in the following referred to as adhesive promoting protein (APP) on the bacteria surface.
(b) The APP is added while simultaneously administering lactic acid bacteria thus increasing the adhesion of bacteria cells.
(c) Cultivation conditions and treatment of the bacteria for oral administering can be modified to give maximum production of APP.
(d) The process for efficient production of APP can be applied to other bacterialstrains to be used for colonising the oesophagus and/or gastro intestinal tract.

The invention is illustrated further with reference to the following non-limiting examples, relating to experiments with animals.

EXAMPLE 1

The cultivation conditions, relating to harvesting and adhesion capacity of lactic acid bacteria were investigated. The adhesion was determined by an in vitro adhesion system using bacteria-free portions of the gastro intestinal tract of mice or pigs. The extent of binding of the bacterial cells was determined using both the radioactive isotop labeling method as well as light microscopy and scanning electron microscopy. Adhesion decreases markedly with subcultering especially in normally used media for culturing lactic acid bacteria. The addition of elevated levels of saccharides enhanced adhesion by a factor of 3. Brain-heart-infusion media normally contains 0.2% glucose. The bacterial cells show no adhesion after having been subcultured in complex nutrient On the other hand a defined casamino acid (CAS) medium with the addition of 2% sucrose resulted in lactic acid bacteria having excellent adhesion capacity to the epithelial cells in the gastro intestinal tract. (Table 1). Other types of sugar, e.g. glucose and lactose, may be used as well as sucrose. Other amino acid compositions different from the casamino acid may also be used. Bacterial cells cultured in a complex medium could adhere if processed to preserve APP with cells. This is further illustrated in example 2.

EXAMPLE 2

The use of the CAS medium with enhanced levels of saccharides enabled a proteinaceous compound APP which promotes adhesion produced by the lactic acid bacteria to be harvested in the supernatant after cultivation. Several proteinaceous molecules are released from the bacterial cells during growth in CAS medium with enhanced levels of saccharides. Protein fractionation of culture supernatant from lactic acid bacteria grown in CAS-medium, has shown that APP can be identified and isolated.

Once identified this APP was also detected when lactic acid bacteria were cultured in a complex brain heart infusion (BHI) broth. The molecular weight of APP has been determined to approximately 14000 using a FPLC system by Pharmacia. Bacteria which cannot adhere to the gastro intestinal tract are, however, able to adhere in the presence of this APP. Besides which, a four-fold increase is obtained in adhesion of bacteria already possessing an ability to bind, when the APP is added. This APP has been demonstrated using host specific strains of lactic acid bacteria e.g. the genera Lactobacillus and Streptococcus for tissue from the gastro intestinal tract from both mouse and pig.

TABLE

Adhesion of Lactobacillus fermentum to mouse stomach, in vitro

| Medium | Washing of bacteria | Addition of adhesion promoting protein APP | Adhesion |
| --- | --- | --- | --- |
| BHI agar | − | − | + |
| BHI agar | + | − | + |
| BHI broth | − | − | + |
| BHI broth | + | − | − |
| BHI broth + 2% sucrose | − | − | +++ |
| BHI broth + 2% sucrose | + | − | + |
| BHI broth | + | + | +++ |
| CAS broth + 2% sucrose | + | + | ++++ |
| CAS broth + 2% sucrose | + | − | + |

What is claimed is:

1. A method for increasing the specific adhesion of lactic acid bacteria to the stomach and intestines of humans and animals, and promoting the colonization of said bacteria therein, comprising administering the bacteria in the presence of effective amounts of an adhesive promoting protein.

2. A method according to claim 1, characterised in that the adhesive promoting protein is produced by cultivating said bacteria in a defined medium containing one or more forms of sugars of enhanced concentration.

3. A method according to claim 2, characterised in that the adhesive promoting protein is produced in vivo.

4. A method according to claim 2, characterised in that the adhesive promoting protein is produced in vitro.

5. A method according to claim 2, characterised in that cultivation is performed in a casamino acid medium or in other amino acid compositions with the addition of forms of sugars of enhanced concentration.

6. A method according to claim 2, characterised in that cultivation is performed in a medium containing sucrose and/or glucose of enhanced concentration.

7. A method according to claim 2, characterised in that cultivation is performed in a medium with the addition of lactose of enhanced concentration.

8. A bacterial composition having improved adhesion for colonization on the stomach and intestines of human and animal hosts comprising:
 (a) a host specific lactic acid bacteria; and
 (b) an adhesive promoting protein prepared by cultivating lactic acid bacteria in a medium containing a sugar or sugars in enhanced concentration.

9. A composition according to claim 8 to increase the adhesion of bacteria to the stomach and intestines of humans and animals, characterised in that the preparation contains non-pathogenic bacteria cultivated in a medium containing sugar types of enhanced concentration for the production of adhesive promoting protein so that the preparation contains the adhesive promoting protein formed during cultivation.

10. A composition according to claim 8, characterised in that the adhesive promoting protein prepared separately is added to the preparation.

11. A composition according to claim 8, to increase the adhesion of bacteria to the stomach and intestines of humans and animals, characterised in that the preparation contains non-pathogenic bacteria cultivated in a medium containing sugar types of enhanced concentration for the production of adhesive promoting protein, and adhesive promoting protein, in combination.

* * * * *